United States Patent
Winterowd et al.

(10) Patent No.: US 9,606,098 B2
(45) Date of Patent: Mar. 28, 2017

(54) MOISTURE INDICATOR FOR WOOD SUBSTRATES

(71) Applicant: WEYERHAEUSER NR COMPANY, Federal Way, WA (US)

(72) Inventors: Jack G. Winterowd, Puyallup, WA (US); Erik M. Parker, Meridian, ID (US); Malinda J. De Lashmutt, Federal Way, WA (US); Wayne Lindell, Tacoma, WA (US); Tri Tran, Tacoma, WA (US)

(73) Assignee: Weyerhaeuser NR Company, Seattle, WA (US)

( * ) Notice: Subject to any disclaimer, the term of this patent is extended or adjusted under 35 U.S.C. 154(b) by 60 days.

(21) Appl. No.: 13/853,373

(22) Filed: Mar. 29, 2013

(65) Prior Publication Data

US 2014/0295561 A1 Oct. 2, 2014

(51) Int. Cl.
| | |
|---|---|
| *G01N 33/46* | (2006.01) |
| *B05D 5/06* | (2006.01) |
| *B05D 7/06* | (2006.01) |
| *B32B 37/14* | (2006.01) |
| *B32B 33/00* | (2006.01) |

(52) U.S. Cl.
CPC .............. *G01N 33/46* (2013.01); *B32B 33/00* (2013.01); *B32B 2317/16* (2013.01)

(58) Field of Classification Search
CPC . G01N 33/46; B05D 5/06; B05D 7/06; B32B 37/14
USPC .................. 156/71; 427/385.5, 393; 436/39; 422/425–426
See application file for complete search history.

(56) References Cited

U.S. PATENT DOCUMENTS

| | | | | |
|---|---|---|---|---|
| 4,558,019 A * | 12/1985 | Kotliar | .................. | C04B 35/013 501/101 |
| 4,764,446 A * | 8/1988 | Croucher | ............... | G03G 9/135 430/115 |
| 4,880,465 A * | 11/1989 | Loria et al. | ................. | 106/31.13 |
| 4,994,322 A * | 2/1991 | Delgado | .................... | C08J 9/32 428/343 |
| 5,300,415 A * | 4/1994 | Sato | ........................ | G03C 1/002 430/513 |
| 5,376,501 A * | 12/1994 | Marien et al. | ................. | 430/257 |
| 5,438,796 A * | 8/1995 | Nathan | .................. | A01G 9/006 47/66.6 |
| 5,460,874 A * | 10/1995 | Rao | ........................... | 428/32.23 |
| 5,596,027 A * | 1/1997 | Mead et al. | ................... | 523/161 |
| 5,677,048 A * | 10/1997 | Pushaw | ..................... | B32B 5/18 428/320.2 |
| 5,726,221 A * | 3/1998 | Alexiou | ................. | C09D 10/00 106/31.64 |
| 5,891,562 A * | 4/1999 | Rutz et al. | .................. | 428/304.4 |
| 6,133,342 A * | 10/2000 | Mizobuchi et al. | .......... | 523/161 |
| 6,174,938 B1 * | 1/2001 | Miller et al. | .................. | 523/164 |
| 6,478,861 B1 * | 11/2002 | Kwan | .................... | B41M 5/267 106/31.14 |
| 6,531,537 B2 * | 3/2003 | Friel | .................... | B01F 13/1055 524/247 |
| 6,646,058 B1 * | 11/2003 | Koger | ........................... | 525/301 |

(Continued)

*Primary Examiner* — Arlen Soderquist
(74) *Attorney, Agent, or Firm* — Perkins Coie LLP

(57) ABSTRACT

A moisture content indicator for visually indicating the moisture content of a wood substrate and methods of making the moisture content indicator are provided.

32 Claims, 5 Drawing Sheets
(5 of 5 Drawing Sheet(s) Filed in Color)

*SAMPLE A*

*12.0% MC*

*SAMPLE B*

*5.0% MC*

(56) References Cited

U.S. PATENT DOCUMENTS

| | | | |
|---|---|---|---|
| 6,655,315 B1* | 12/2003 | Gattiglia | G01N 31/222 116/200 |
| 6,930,135 B2* | 8/2005 | Chung et al. | 523/160 |
| 7,435,694 B2* | 10/2008 | Kajander | 442/417 |
| 7,717,992 B2* | 5/2010 | Klots et al. | 106/31.65 |
| 8,054,323 B2* | 11/2011 | Peters et al. | 347/221 |
| 8,168,266 B2* | 5/2012 | Klots et al. | 427/557 |
| 2003/0176534 A1* | 9/2003 | Chung et al. | 523/160 |
| 2003/0176535 A1* | 9/2003 | Chung et al. | 523/160 |
| 2004/0192148 A1* | 9/2004 | Kajander | 442/417 |
| 2005/0107492 A1* | 5/2005 | Sukhna | 523/160 |
| 2005/0154109 A1* | 7/2005 | Li et al. | 524/409 |
| 2006/0068191 A1* | 3/2006 | Goto | C09J 7/0242 428/313.3 |
| 2006/0090670 A1* | 5/2006 | Klots et al. | 106/31.65 |
| 2006/0140991 A1* | 6/2006 | Makino | A61K 9/107 424/400 |
| 2007/0012414 A1* | 1/2007 | Kajander et al. | 162/129 |
| 2007/0043129 A1* | 2/2007 | Chou | C08F 291/00 521/54 |
| 2007/0059444 A1* | 3/2007 | Hladik | B41M 5/52 427/180 |
| 2007/0065749 A1* | 3/2007 | Kasperchik et al. | 430/270.1 |
| 2007/0157702 A1* | 7/2007 | Hamada | G01N 31/222 73/29.04 |
| 2008/0015107 A1* | 1/2008 | Elmasry | B41M 5/3372 503/200 |
| 2008/0097018 A1* | 4/2008 | Stratton | 524/425 |
| 2008/0179562 A1* | 7/2008 | Quincy | 252/8.91 |
| 2008/0245289 A1* | 10/2008 | Shiraishi | B32B 5/00 116/206 |
| 2008/0254240 A1* | 10/2008 | Niu et al. | 428/32.16 |
| 2009/0214837 A1* | 8/2009 | Albenice et al. | 428/195.1 |
| 2010/0245524 A1* | 9/2010 | Peters et al. | 347/221 |
| 2011/0059841 A1* | 3/2011 | Stratton | 502/158 |
| 2011/0318547 A1* | 12/2011 | Zhu et al. | 428/195.1 |
| 2012/0263659 A1* | 10/2012 | Subkowski | A23G 3/36 424/54 |
| 2013/0085222 A1* | 4/2013 | Fasano | C09C 1/3676 524/522 |

* cited by examiner

SAMPLE A 12.0% MC

SAMPLE B 5.0% MC

SAMPLE A 8.0% MC

SAMPLE B 5.0% MC

INITIAL TEST SPECIMENS

SAMPLE A   SAMPLE B 5.3% MC            5.3% MC

ONE HOUR OF SUBMERSION

SAMPLE A | SAMPLE B 12.2% MC | 5.3% MC

TWO HOURS OF SUBMERSION

SAMPLE A | SAMPLE B 14.6% MC | 5.3% MC

ONE HOUR OF REDRY

SAMPLE A 12.1% MC

SAMPLE B 5.3% MC

TWO HOURS OF REDRY

SAMPLE A 10.4% MC

SAMPLE B 5.3% MC

THREE HOURS OF REDRY

SAMPLE A  SAMPLE B 8.9% MC        5.3% MC

FOUR HOURS OF REDRY

SAMPLE A  SAMPLE B 8.0% MC        5.3% MC

MOISTURE INDICATOR FOR WOOD SUBSTRATES

BACKGROUND

Oriented strand board (OSB) panels are wood structural panels commonly used in building construction as subflooring, wall sheathing, and roof decking. Because OSB panels are used as a sub-material, it is important that the moisture content of the OSB panels is at a threshold level of about 8-10% prior to installation of decorative materials (e.g. hardwood flooring) on top of the OSB panels. OSB panels are frequently exposed to precipitation during the construction process, and it is therefore necessary to determine that the moisture content of the OSB panels is at an acceptable level before installation of the top material.

Builders currently assess the moisture content of OSB panels by use of various moisture meters. Access to the moisture meters may be limited, and/or due to time constraints or other factors, builders often do not conduct the moisture measurements. As a result, adjacent decorative materials are frequently installed directly onto OSB panels that have a relatively high moisture content.

In many cases adjacent decorative materials, such as hardwood flooring, are mechanically fastened to OSB panels by use of cleats, staples or nails. If the decorative material is relatively dry and the OSB panels are relatively wet, then the decorative material will tend to expand as it absorbs moisture from the OSB panels, and the OSB panels will tend to shrink as they dry. The opposing movement of the rigidly connected materials tends to damage and weaken the mechanical bonds. Shrinkage of the OSB panels can also decrease their ability to rigidly hold imbedded fasteners. This situation commonly results, for example, in squeaky floors that must be repaired by the builder.

Installation of OSB panels having too high of a moisture content results in poor quality construction and increased costs. Thus, a technology is needed that allows the builder to quickly and easily assess whether the moisture content of OSB panels is at a threshold level of about 10% or below.

The present disclosure is directed to a moisture content indicator for visually determining the moisture content of a wood substrate, including OSB panels and other types of wood structural panels and structural members.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

The present disclosure addresses the problem of assessing the moisture content of a wood substrate. In one aspect, the present disclosure is directed to a moisture content indicator for visually determining the moisture content of a wood substrate, the moisture content indicator includes a transition layer composition comprising an opaque polymer, a surfactant, and a binding agent.

In one aspect, the present disclosure optionally includes a color composition layer disposed between the transition layer composition and the wood substrate. The color composition layer includes one or more colored pigment(s) and a second binding agent. The colored pigment is visible when the moisture content of the wood substrate is above a selective level In one aspect of the present disclosure, the transition layer composition includes one or more colored pigment(s). Such colored pigment(s) can be included in the transition layer composition whether or not the optional color layer composition is used. The colored pigment is visible when the moisture content of the wood substrate is above a selected level.

In one aspect of the present disclosure, text and/or indicia is incorporated into or on the word substrate or the colored pigment of the color composition layer are arranged to compose the text/indicia. The text/indicia is visible when the moisture content of the substrate in above a selected level.

In one aspect of the present invention, the indicia can be composed of letters, symbols; designs icons, patterns, etc. that is visible when the moisture contend of the wood substrate is above a selected level.

In one aspect, the present disclosure is directed to methods of making a moisture content indicator.

DESCRIPTION OF THE DRAWINGS

The patent or application file contains photographs presented in color. Copies of this patent or patent application publication with color photographs will be provided by the Office upon request of the necessary fee.

The foregoing aspects and many of the attendant advantages of this invention will become more readily appreciated as the same become better understood by reference to the following detailed description, when taken in conjunction with the accompanying drawings, wherein.

DETAILED DESCRIPTION

Figure 1A:
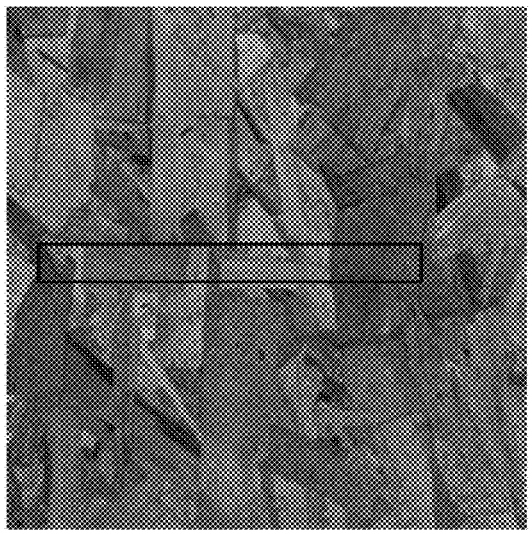
FIGS. 1(a) and 1(b) are illustrations of the appearance of a moisture content indicator of the present disclosure when the moisture content of the wood substrate is about 12% and 8%, respectively.
Figure 1A:
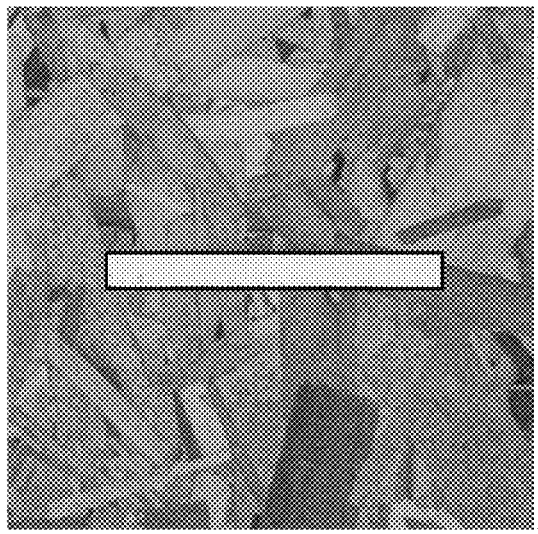

Unless specifically defined herein, all terms used herein have the same meaning as they would to one of skill in the art.

In one aspect, the present disclosure provides a moisture content indicator for visually determining the moisture content of a wood substrate. The moisture content indicator can include a transition layer composition composed of an opaque polymer, a surfactant, and a binding agent. The moisture content indication can also optionally include a color layer composition including one or more colored pigment(s) and a binding agent. The optional color layer composition is positionable between the transition layer and the wood substrate. However, in a more basic form of the present disclosure, the transition layer is mounted to a wood substrate without the presence of the color layer composition.

The transition layer composition of the moisture content indicator includes an opaque polymer, a surfactant, and a binding agent. As used here, the term "opaque polymer" refers to aqueous styrene-acrylic microsphere dispersions. Opaque polymers are known. Suitable opaque polymers include Ropaque™ Ultra available from The Dow Chemical Company of Midland, Mich., and Celocor™, available from Arkema Inc. of King of Prussia, Pa. Generally, opaque polymers comprise microsphere particles having a hollow core. When an opaque polymer is in a wet state, the hollow core is filled with water causing microsphere particles to be substantially translucent or transparent. As the opaque polymer dries, water in the core is replaced with air, and the air scatters the light impinging on the hollow core, transitioning the polymers into an opaque or white appearance.

In some embodiments, the transition layer composition includes an opaque polymer in a concentration in the range of about 5% w/w to 70% w/w. In some embodiments, the transition layer includes an opaque polymer in a concentration of about 20-45% w/w.

In some embodiments, the transition layer composition comprises a surfactant in a concentration range of about 0.1-40%. Surfactants suitable for use in the present disclosure can be cationic, anionic, amphoteric, or nonionic.

Anionic surfactants can include sulphates, sulphonates, phosphates, and carboxylic acids. Examples of anionic surfactants include sodium lauryl sulphate, perfluorooctanesulphonate, sodium stearate, ammonium lignosulphonate, and sodium lauryl phosphate.

Amphoteric surfactants can include proteins, such as lecithin, and betaines, such as cetyl betaine and cocamidopropyl betaine.

Nonionic surfactants can include alkyl ethers, alkylphenol ethers, alkyl phenols, alkyl glucosides, fatty alcohols, polysorbates, and silicones, e.g., poly(ethylene glycol), poly (propylene glycol), PEG-10 glyceryl stearate, 4-octylphenol polyethoxylate, nonylphenol, decyl glucoside, isostearyl alcohol, polyoxyethlene (20) sorbitan monolaurate, polyoxyethlene (20) sorbitan monopalmitate, and various polysiloxanes, such as poly(dimethylsiloxane).

In some embodiments, the surfactant used in the transition layer composition is a polymer that is resistant to diffusion when the moisture content indicator is in a wet state.

Polymeric surfactants suitable for use in the transition layer composition include polymers with multiple carboxylic acid functional groups that have been neutralized with basic compounds. Polymeric surfactants can include salts of anionic polysaccharides and polyacrylic acid.

In some embodiments, the polymeric surfactants are salts of alginic acid such as the sodium salt of alginic acid formed by addition of sodium hydroxide to an alginic acid solution, the triethanolamine salt of alginic acid formed by addition of triethanolamine to an alginic acid solution, the morpholine salt of alginic acid formed by addition of morpholine to an alginic acid solution.

In some embodiments, the salts of polyacrylic acid can be used as an anionic polymeric surfactant. In some embodiments, polymeric cationic surfactants can be used as a polymeric surfactant. One example of a suitable polymeric surfactant is a salt formed by combining polyethylene imine with an acid, such as hydrochloric acid or acetic acid. Other examples of suitable polymeric surfactants are chitosan, a biopolymer comprised of glucosamine and N-acetylglucosamine units, combined with acids, such as hydrochloric acid or acetic acid to form a salt that can function as a polymeric surfactant suitable for use in the transition layer composition.

In some embodiments, the transition layer composition includes a surfactant in a concentration of about 1% to about 20% w/w.

Suitable binding agents used in the transition layer composition of the moisture indicator are generally water-insoluble polymeric binders and are described below as also suitable for use in the color layer composition of the moisture indicator.

In some embodiments, the transition layer composition includes a binding agent in a concentration in the range of about 5% w/w to 95% w/w. In some embodiments, the transition layer composition includes a binding agent in a concentration of about 40-85% w/w.

In some embodiments, the transition layer composition can further include viscosity-enhancing agents, pH adjusting agents, preservatives, diluents, fillers, catalysts and/or other minor components that might improve the storage life or processing characteristics of the liquid formulation used as a precursor to form the transition layer composition.

In accordance with the present disclosure, the moisture content range of the wood substrate is indicated by the appearance of the moisture content indicator. In some embodiments, the moisture content indicator of the present disclosure transitions between a translucent or transparent appearance wherein the background wooden substrate is visible, and an opaque white appearance when the moisture content of the wood substrate is from about 9% to about 10% or lower than about 9% ("transition point"). Above this transition point, due to its moisture content, the wood substrate is said to be in "wet" condition; and below this transition point, due to its moisture content, the wood substrate is said to be in "dry" condition.

In some embodiments, the moisture content indicator exhibits a translucent or transparent appearance when the moisture content of the wood substrate is greater than about 10%. For example, the moisture content indicator of the present disclosure exhibits a translucent or transparent appearance when the moisture content of the wood substrate is from about 10% to about 16% or more, for example about 10%, 11%, 12%, 13%, 14%, 15%, 16%, and greater.

In some embodiments, the moisture content indicator of the present disclosure exhibits a white/opaque appearance when the moisture content of the wood substrate is less than about 9%. For example, the moisture content indicator of the present disclosure exhibits a white/opaque appearance when the moisture content of the wood substrate is from about 5% to about 9%, for example about 5%, 6%, 7%, 8%, and 9%.

As stated above, embodiments of the present disclosure can optionally utilize a color layer composition beneath the transition layer. The color layer composition of the moisture content indicator can include one or more colored pigment(s) and a binding agent to secure the colored pigment(s) to the wooden substrate. In some embodiments, the colored pigment(s) are of a dark or vibrant color. Examples of some suitable colored pigment(s) include copper phthalocyanine blue (also known as Pigment Blue 15), halogenated copper phthalocyanine (also known as Pigment Green 7), barium lithol red (Pigment Red 49:1), toluidine red (Pigment Red 3), calcium lithol rubine (Pigment Red 57:1), quinacridone quinine (Pigment Orange 49), perylene reds (including Pigment Red 224), benzimidazolone pigments (including Pigment Red 242), thioindigoid reds (including violet shade Pigment Red 88), carbazole violet (including Pigment Violet 23), monoarylide yellows (including Hansa Yellow G), diarylide yellows (including yellow 12), benzimidazolone yellows (including Pigment Yellow 120), heterocyclic yellows (including Pigment Yellow 138), orthonitraniline orange (Pigment Orange 2), carbon black, and Nathol Orange (Pigment Orange 38), or mixtures of these colored pigments. Pigments can also include inorganic pigments, such as iron oxide or lead chromate, or natural pigments such as flavonoids or carotenoids.

Suitable binding agents for the transition layer composition and for the color layer composition are known in the art and include, but are not limited to, polymers and/or resins such as alkyd resins, polyurethanes, epoxies, isocyanates, phenolics, urea/formaldehyde resins, melamine/formaldehyde resins; aqueous latex products such as acrylic emulsions or styrene/butadiene emulsions; and polymeric or oligomeric dispersions or solutions. Examples of suitable acrylic binding agents include Ray Tech® 51. Ray Tech® 49. Raykote® 78070. and Raycryl® 1020. available from Specialty Polymers Inc of Woodburn, Oreg., and a styrene/butadiene emulsion known as Rovene® 4021. available from Mallard Creek Polymers Inc. of Charlotte, N.C.

In some embodiments, the color layer composition of the moisture indicator comprises colored pigment(s), as well as an aqueous binding agent, a wetting agent, and/or surfactant. Wetting agents/surfactants may improve the phase stability of the color layer composition prior to application to the wood substrate. Suitable wetting agents/surfactants include alkyd resins, acrylic resins and polyester resins.

Compositions comprising colored pigment, an aqueous binding agent, and, optionally, a wetting agent, are commonly known in the art as "pigment dispersions." Suitable colored pigment dispersions for use in the present disclosure include a pigment dispersion of a blue color, for example Sunfast® Blue 15:3. available from Sun Chemical Corporation of Parsippany, N.J., and a pigment dispersion of black color, such as 84BD1079 (black) manufactured by Flint Group Pigments, Resins and Chips of Elizabethtown, Ky.

In some embodiments the color layer composition includes colored pigment(s) in a concentration in a range of about 0.1% w/w to about 95% w/w. In some embodiments the color layer includes colored pigment(s) in a concentration of about 2% w/w to about 20% w/w.

In some embodiments the color layer composition includes a binding agent in a concentration in a range of about 0.1% w/w to about 95% w/w. In some embodiments the color layer composition includes a binding agent in a concentration of about 5% w/w to about 80% w/w.

In some embodiments, the color layer composition further includes viscosity-enhancing agents, pH adjusting agents, preservatives, diluents, fillers, catalysts and/or other minor components that might improve the storage life or processing characteristics of the liquid formulation used as a precursor to form the color layer composition. In some embodiments, the viscosity-enhancing agent is an anionic acid-containing acrylic emulsion. Suitable viscosity-enhancing agents are known in the art and include, for example, Acrysol™ ASE-60 and Acrysol™ TT-615. available from the Dow Chemical Company of Midland, Mich.

In accordance with the present disclosure, the moisture content of the wood substrate is indicated by the appearance of the moisture content indicator. In some embodiments, the moisture content indicator of the present disclosure transitions between a colored appearance and an opaque appearance when the moisture content of the wood substrate is from about 9% to about 10%.

In some embodiments, the moisture content indicator exhibits a colored appearance when the moisture content of the wood substrate is greater than about 10%. For example, the moisture content indicator of the present disclosure exhibits a colored appearance when the moisture content of the wood substrate is from about 10% to about 16% or more, for example about 10%, 11%, 12%, 13%, 14%, 15%, 16%, and greater.

In some embodiments, the moisture content indicator of the present disclosure exhibits a white/opaque appearance when the moisture content of the wood substrate is less than about 9%. For example, the moisture content indicator of the present disclosure exhibits a white/opaque appearance when the moisture content of the wood substrate is from about 5% to about 9%, for example, about 5%, 6%, 7%, 8%, and 9%.

While not being bound by any theory, it is hypothesized that the opaque polymer of the transition layer composition transitions from a state of translucence or transparency to a state of opacity as a function of the moisture content of the wood substrate. When the moisture content of the wood substrate is above about 10% or other pre-selected moisture level, the transition layer composition is transparent, revealing the underlying substrate or the color of a color layer composition disposed between the transition layer and the substrate. When the moisture content of the wood substrate is below about 9%, the transition layer composition is opaque and white, hiding the underlying substrate or the color layer composition.

Also without being bound by a particular theory, it is hypothesized that the surfactant level and type help to determine the critical moisture content value associated with the visual transition of the indicator. In general, higher levels of surfactant will cause the visual transition point to shift to a lower moisture content value in the wood. Likewise, thinner transition layers will be associated with visual transition points at a lower moisture content value in the wood.

Methods of making a moisture indicator for visually determining the moisture content of a wood substrate are provided. One method includes: applying the transition layer composition including an opaque polymer, a surfactant, and a second binding agent, onto a wood substrate.

The method can further include the step of drying the transition layer composition. In some embodiments, the dried transition layer composition has a basis weight of about 0.1 g/ft$^2$ to about 100 g/ft$^2$. In some embodiments, the dried transition layer composition has a basis weight of about 5 g/ft$^2$ to about 50 g/ft$^2$.

In some embodiments, the transition layer composition is applied in liquid form. In a production setting, a manufacturer may not want to encumber or slow down an existing finishing line for a wood product with the drying times that are required with application of water-based formulations of the transition layer composition. In some embodiments, the transition layer composition is applied to a thin substrate, such as a paper or fabric substrate. In some embodiments, an adhesive, such as a pressure-sensitive adhesive, is applied to the bottom surface of the substrate in order to allow the substrate comprising the moisture content indicator of the present disclosure to be instantly applied to a wood substrate.

FIG. 1(a) illustrates the transition layer composition as applied to a wood substrate. In sample A, the moisture content of the wood substrate is 12%. With that moisture content level, the transition layer composition is substantially translucent or transparent so that the color and composition of the underlying wood substrate shows through the transition layer composition. The location of the transition layer composition can be indicated by a black or other colored rectangular border. Of course, other methods or means can be used to identify the location of the transition layer composition. In sample B of FIG. 1(a), the moisture content of the wood substrate is 5%. At this moisture content, the transition layer composition has transitioned into a state of opacity. As such, the transition layer composition appears as white in color.

Figure 1B:
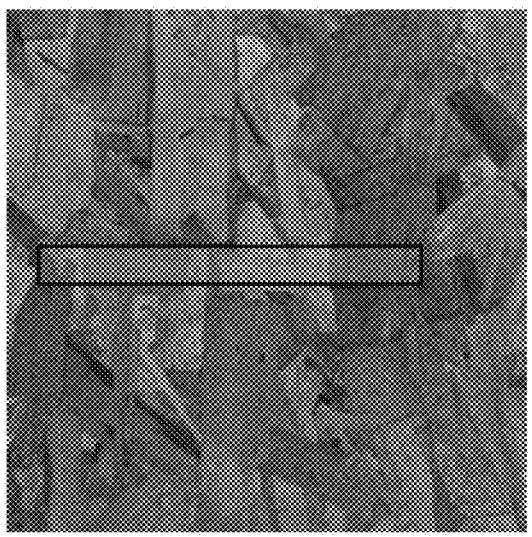
Figure 1B:
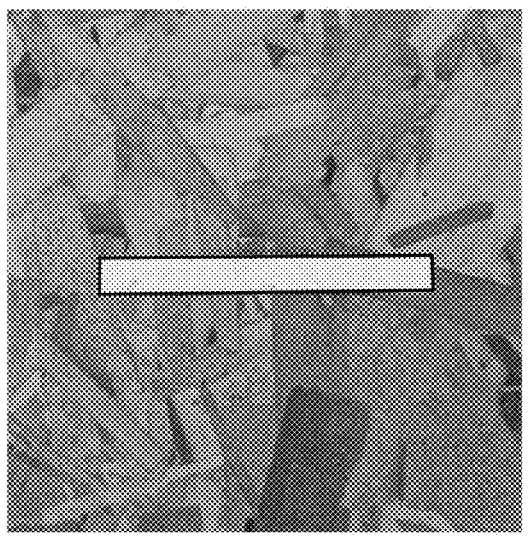

Next, referring to FIG. 1(b), the moisture content in sample A is at 8%. At this percentage, the state of transparency of the transition layer composition is diminishing and starting to move to a state of opacity. However, the underlying composition of the wood substrate is still visible through the transition layer composition. However, as shown in sample B of FIG. 1(b), when the moisture content of the wood substrate has lowered to 5%, the transition layer composition has reached a state of opacity so that the transition layer composition appears to be white in color.

In another aspect of the present disclosure, methods of making a moisture content indicator for visually determining the moisture content of a wood substrate are provided, which include both the color layer composition and the transition layer composition. Each of the methods includes the steps of: a) first applying a color layer composition including one or more colored pigment(s) and a first binding agent to a substrate; b) drying the color layer composition; and c) applying a transition layer composition including an opaque polymer, a surfactant, and a second binding agent onto the color layer composition.

In some embodiments, the dried color layer composition has a basis weight of about 0.1 g/ft$^2$ to about 100 g/ft$^2$. In some embodiments, the dried color layer composition has a basis weight of about 5 g/ft$^2$ to about 50 g/ft$^2$.

In some embodiments, the methods further comprise the step of drying the transition layer composition after application on the color layer composition. In some embodiments, the dried transition layer composition has a basis weight of about 0.1 g/ft$^2$ to about 100 g/ft$^2$. In some embodiments, the dried color layer composition has a basis weight of about 5 g/ft$^2$ to about 50 g/ft$^2$.

In some embodiments, the color layer composition and the transition layer composition are applied in liquid form directly to the wood substrate. In a production setting a manufacturer may not want to encumber or slow down an existing finishing line for a wood product due to the required drying times that are associated with application of water-based formulations of the color layer composition and the transition layer composition. In some embodiments, the color layer composition and the transition layer composition are sequentially applied to a thin substrate, such as a paper or fabric substrate. In some embodiments, an adhesive, such as a pressure-sensitive adhesive, is applied to the bottom surface of the substrate in order to allow the substrate comprising the moisture content indicator of the present disclosure to be instantly and conveniently applied to a wood substrate.

In some embodiments one or both layers of the coating system could be applied to the wooden substrate during the production of the wooden substrate. For instance, either the transition layer composition or the color and transition layer composition of the coating system could be applied to a strand mat prior to pressing in the production of OSB.

In some embodiments of the methods of the present disclosure, the color layer composition comprises a colored pigment at a concentration in the range of about 0.1% to about 95%. In some embodiments, the color layer composition comprises a colored pigment at a concentration of about 2-20%.

In some embodiments of the methods of the present disclosure as noted above, the transition layer composition comprises an opaque polymer at a concentration in the range of about 5% w/w to about 70% w/w. In some embodiments, the transition layer composition comprises an opaque polymer at a concentration of about 20% w/w to about 45% w/w.

Embodiments of the present invention can optionally also include color pigments in the transition layer composition. Such color pigment(s) can be employed in the transition layer composition whether or not the optional color layer composition is utilized. Typically, relatively low levels of pigment(s) would be utilized for this purpose. As a non-limiting example, the concentration of the one or more pigment(s) can be in the range of about 1-10%.

The composition of the color pigment(s) utilized in the transition layer composition can be the same or similar to the pigment compositions described above with respect to the color layer composition. In this regard, pigment(s) can be organic or inorganic.

If a color pigment is employed in the transition layer composition and if no color layer composition is utilized, when the moisture content of the wood substrate is in "wet" condition, for example, having a moisture content greater than 10%, the color of the indicator will be the result of the color of the underlying wood substrate combined with the color of the pigment(s) in the transition layer composition. However, if the moisture content of the wood substrate is below the transition point, for example about 9%, so that the wood substrate is in "dry" condition, the color of the indicator will correspond to the color of the pigment(s) utilized in the transition layer composition.

In a situation in which a color layer composition is utilized and a color pigment is employed in the transition layer composition, when the wood substrate is in "wet" condition, the color of the indicator will be the resulting color of the combination of the color of the pigment(s) utilized in the transition layer composition and the color of the pigment(s) in the color layer composition. On the other hand, when the wood substrate is in "dry" condition, the color of the indicator would be the color of the pigment(s) utilized in the transition layer composition. For example, if a yellow colored pigment is utilized in the transition layer composition and a blue color composition is utilized in the color layer composition, when the wood substrate is in "wet" condition the color indicator would be green, resulting from the combination of the yellow colored pigment in the transition layer composition and the blue colored pigment in the color layer composition. However, when the wood substrate is in "dry" condition, the color indicator will be yellow, since the color of the color layer composition will not be visible, and only the color of the transition layer composition will be visible.

Embodiments of the present invention can also include text and/or indicia rather than color to indicate a moisture content of a wood substrate. In this regard, text such as the word "wet" or the phrases "moisture content over 10%" or "moisture content too high" could be made to appear when the moisture content of the wood substrate is above the set transition level, in other words, when the wood substrate is in "wet" condition. The word or words of the text could be patterned into the color indicator so that the word or words appear in color due to the transition layer composition being in a state of transparency or translucence. However, when the moisture level of the wood substrate is below the transition level, the transition layer composition becomes opaque, thereby hiding the underlying text.

As an alternative implementation, the desired text could be printed on a wood substrate or onto a paper sized fabric substrate that is in turn attached to the wood substrate. Therefore, the printed text could be overlaid with a transition layer composition so that when the wood substrate is in wet condition, the text appears through the transition layer composition, but is hidden from view if the moisture level is low enough to cause the transition layer composition to transform into an opaque state. Moreover, a color pigment could be employed in the transition layer composition so that when the moisture level causes the transition layer composition to become opaque, the transition layer is not only opaque but also colored.

As a further aspect of the present disclosure, the text could be replaced by an indicia, for instance, one or more letters, a design, icon, symbol, pattern, etc., that is indicative of the moisture content of the wood substrate or indicates that the wood substrate is of a moisture content above the transition level or that the wood substrate is of a moisture content too high to be utilized for its intended purpose. For example, the symbol could be indicative of a particular intended use of the wood substrate, and a diagonal line is extended there over to indicate that the wood substrate should not be employed for such use. Thus, the initial symbol could be more universal than if English text or text in a particular language were employed.

Wood substrates suitable for use in the present disclosure include, but are not limited to, oriented strand board, plywood, particleboard, fiberboard, laminated veneer lumber (LVL), long strand lumber (LSL), oriented strand lumber (OSL), parallel strand lumber (PSL), glulam, solid sawn lumber, and other wood substrates. The wood substrates of the present disclosure are useful in the residential construction industry, furniture building, and other applications where the moisture content of the wood substrate is important.

EXAMPLE

The following example is provided for the purpose of illustrating, not limiting, the present disclosure.

This example provides a method of making a wood substrate comprising a moisture indicator.

Two oriented strand boards ("OSB") having dimensions of 8" by 8" by ⅜" were used in this example. The OSBs were treated as described below.

Step 1. A 5" by 0.5" open-stenciled area in the center of an OSB was sprayed with Formula I, 0.5 grams on a wet basis. The applied Formula I was allowed to dry at a temperature of 20° C., relative humidity 50%, for a period of 30 minutes.

Step 2. The open-stenciled area treated in step 1 was sprayed with Formula II, 0.5 grams on a wet basis. The applied spray was allowed to dry at a temperature of 20° C., relative humidity 50%, for a period of 30 minutes.

Formulas I and II are provided below.

Formula I

| Component | Mass (grams) | Mix Time (minutes) |
|---|---|---|
| SUN BCD-9448[a] blue pigment dispersion (aqueous) | 4.0 | |
| Water | 91.0 | 5 |

-continued

| Component | Mass (grams) | Mix Time (minutes) |
|---|---|---|
| 50% ACRYSOL ASE60[b] Solution | 5.0 | 5 |
| RAY TECH 1175[c] | 300.0 | 5 |

[a]Sun Chemical Corp (Parsippany, NJ)
[b]The Dow Chemical Company (Midland, MI)
[c]Specialty Polymers Inc. (Woodburn, OR)

Formula II

| Component | Mass (grams) | Mix Time (minutes) |
|---|---|---|
| Water | 50.0 | |
| Alginic Acid | 5.0 | 5 |
| Triethanolamine | 5.0 | 5 |
| CELOCOR Opaque Polymer[d] | 120.0 | 5 |
| 50% ACRYSOL ASE60[b] Solution | 7.0 | 5 |
| RAY TECH 1175[c] | 214.0 | 5 |
| 33.4% ACRYSOL TT615[b] Solution | 1.0 | 5 |

[d]Arkema Inc. (King of Prussia, PA)

Figure 2:
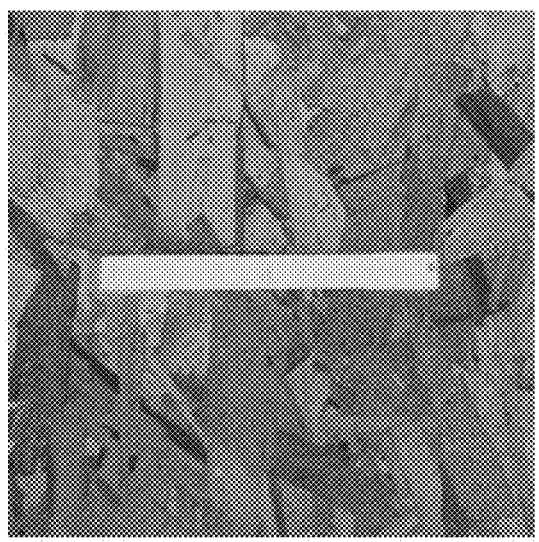
FIG. 2 is an illustration of the appearance of a moisture content indicator of the present disclosure when the moisture content of the wood substrate is about 5.3%.
Figure 2:
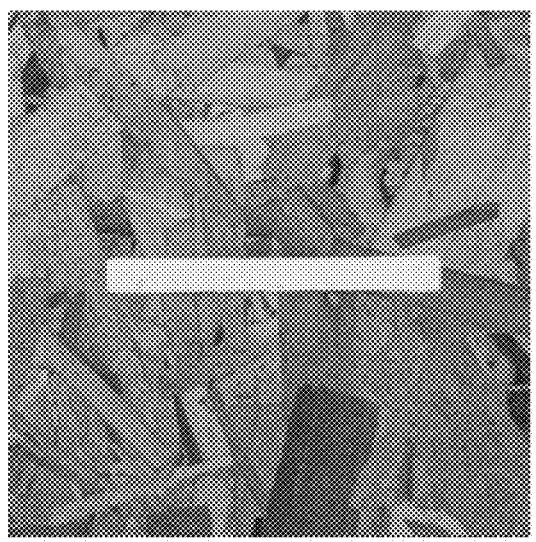

The treated OSB sections were allowed to equilibrate at 20° C., relative humidity 20% for three days. The moisture content was measured and determined to be 5.3%. The samples were photographed. At the beginning of the study, the treated area of each board appeared white/opaque, as illustrated in FIG. 2.

One treated OSB section was submerged in water and dried as described below (Sample A). The other treated OSB section (Sample B) was not submerged in water and was used as a control.

Sample A was measured for mass and submerged under one inch of standing water at a temperature of 20° C. Sample A was removed from the water after one hour, measured for mass, photographed, and returned to submersion under water. This was repeated in one-hour increments for a total immersion time of three hours.

Sample A was then allowed to dry on a wire rack at 20° C., relative humidity of 20%. The sample was measured for mass and photographed at one-hour increments for four hours, and again at 24 hours.

Results

Figure 3A:
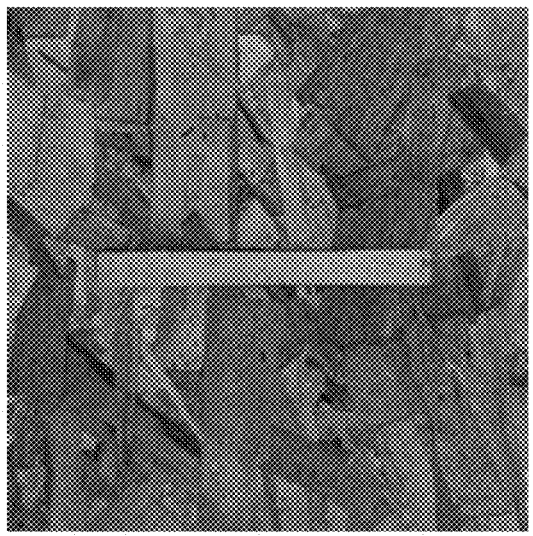
FIGS. 3(a) and 3(b) are illustrations of the appearance of a moisture content indicator of the present disclosure when the moisture content of the wood substrate is about 12.2% and about 14.6%, respectively.
Figure 3A:
Figure 3B:
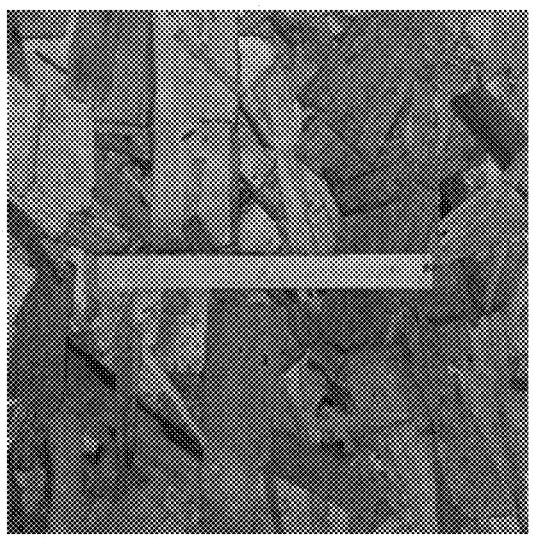
Figure 3B:
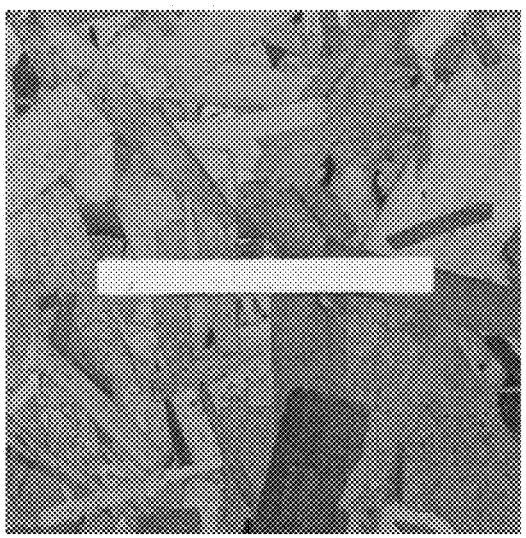
Figure 4A:
FIGS. 4(a) and 4(b) are illustrations of the appearance of a moisture content indicator of the present disclosure when the moisture content of the wood substrate is about 12.1% and about 10.4%, respectively.
Figure 4A:
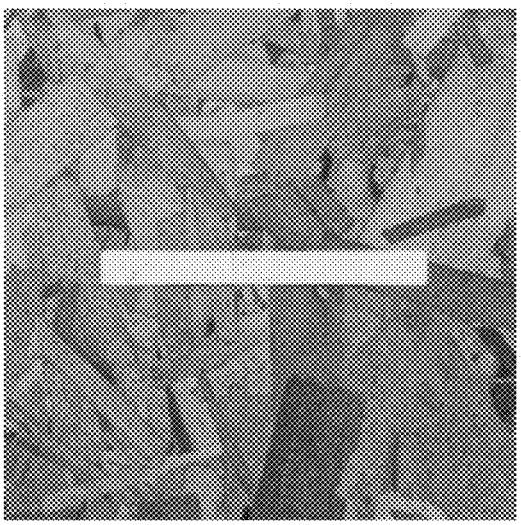
Figure 4B:
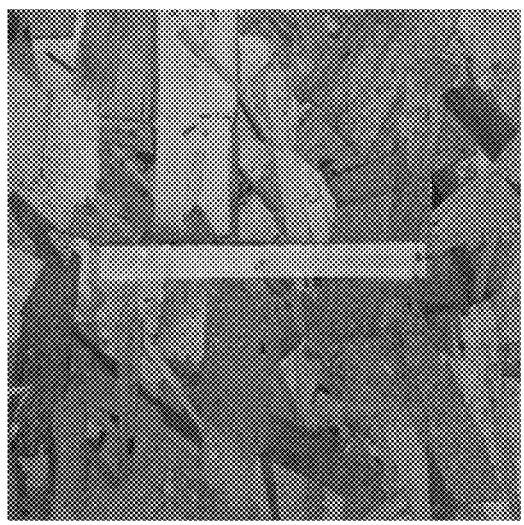
Figure 4B:
Figure 5A:
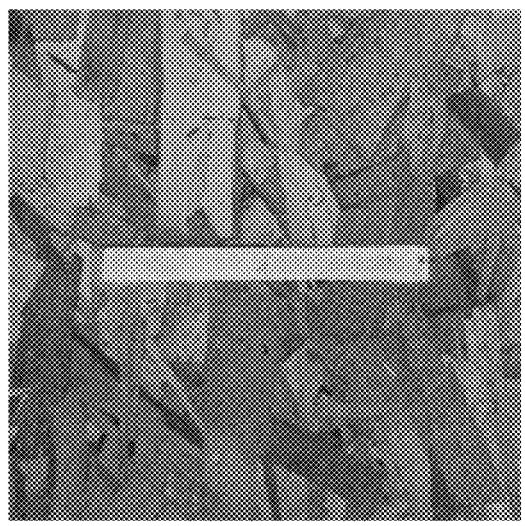
FIGS. 5(a) and 5(b) are illustrations of the appearance of a moisture content indicator of the present disclosure when the moisture content of the wood substrate is about 8.9% and about 8.0%, respectively.
Figure 5A:
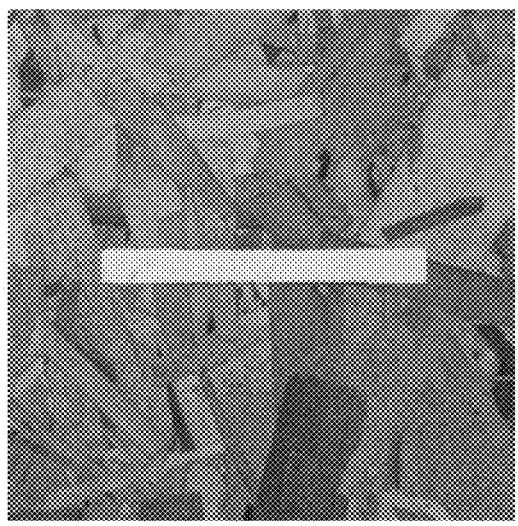
Figure 5B:
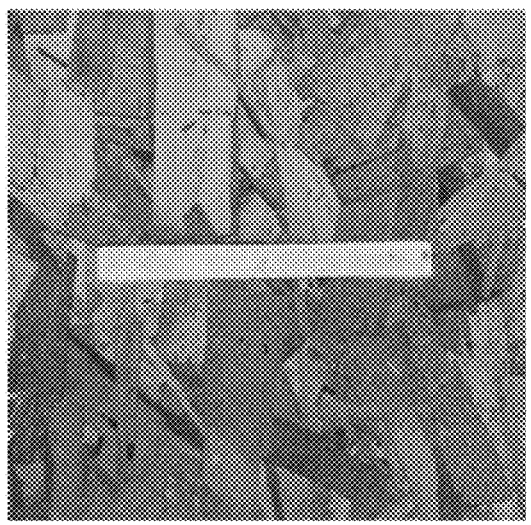
Figure 5B:
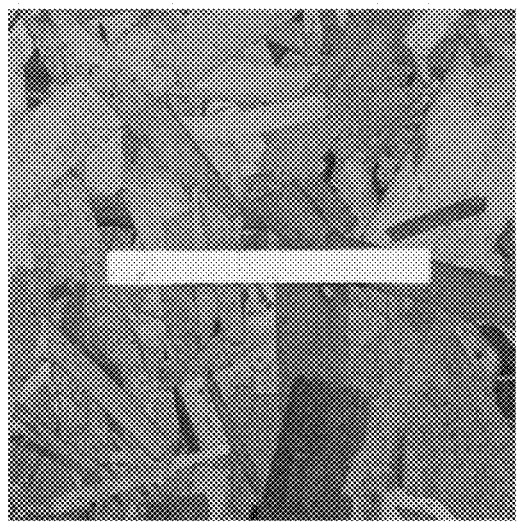

Submersion under water. After one hour of submersion under water, the moisture content of Sample A was determined to be 12.2% and the color of the treated strip was blue. After two hours of submersion, the moisture content was 14.6%, and the color of the treated strip remained blue. The results of submersion under water for one hour and two hours are illustrated in FIGS. 3a and 3b, respectively. After three hours of submersion, the moisture content was 16.2%, and the color of the treated strip remained blue (data not shown).

Drying (T=20° C., R.H.=50%). After one hour of drying, the moisture content of Sample A was determined to be 12.1% and the color of the treated strip was blue. After two hours of drying, the moisture content was 10.4% and the color of the treated strip was a lighter blue, but still distinctly blue. After three and four hours of drying, the moisture content was 8.9% and 8.0%, respectively, and the color of the treated strip became lighter as the drying time was extended. At 8.9% moisture content, the color of the strip was only faintly blue. The results of drying are illustrated in FIGS. 4a, 4b, 5a, and 5b, respectively. cl DISCUSSION The results obtained in Example 1 illustrate that at a moisture content of about 10% or above the treated strip is a distinctly blue color; and at a moisture content of about 9% or below the treated strip is a faint blue to white color. The two-layer moisture indicator described in the present disclosure provides a simple visual indicator of the moisture content of a wood substrate.

While illustrative embodiments have been illustrated and described, it will be appreciated that various changes can be made therein without departing from the spirit and scope of the invention.

The embodiments of the invention in which an exclusive property or privilege is claimed are defined as follows:

1. A moisture content indicator for visually determining the moisture content of a wood substrate, the moisture content indicator comprising a transition layer composition, the transition layer composition comprising (i) an opaque polymer, wherein the opaque polymer is a styrene-acrylic microsphere dispersion and the microspheres of the dispersion have a hollow core; (ii) a polymeric surfactant, wherein the polymeric surfactant is a salt of an anionic polysaccharide; and (iii) a binding agent;
   wherein the transition layer composition is constituted such that the transition layer composition reversibly transitions between a transparent appearance and an opaque white appearance depending upon the moisture content of the transition layer.

2. The moisture content indicator of claim 1, wherein the binding agent of the transition layer is at least one of an alkyd resin, an aqueous latex, and a polymeric or oligomeric dispersion.

3. The moisture content indicator of claim 1, wherein the anionic polysaccharide is alginic acid.

4. The moisture content indicator of claim 3, wherein the transition layer composition is constituted such that the transition layer composition transitions between a colored appearance and an opaque appearance when the moisture content of the wood substrate is from about 9% to about 10%.

5. The moisture content indicator of claim 4, wherein the transition layer composition is constituted such that the transition layer composition exhibits a colored appearance when the moisture content of the wood substrate is greater than about 10%.

6. The moisture content indicator of claim 4, wherein the transition layer composition is constituted such that the transition layer composition exhibits a white/opaque appearance when the moisture content of the wood substrate is less than about 9%.

7. The moisture content indicator of claim 1, wherein the transition layer composition further comprises a color pigment.

8. The moisture content indicator of claim 1, wherein the transition layer composition is constituted such that the transition layer composition transitions between a transparent appearance and an opaque white appearance when the moisture content of the wood substrate is from about 9% to about 10%.

9. The moisture content indicator of claim 8, wherein the transition layer composition is constituted such that the transition layer composition exhibits a white/opaque appearance when the moisture content of the wood substrate is less than about 9%.

10. The moisture content indicator of claim 1, wherein the concentration of the opaque polymer in the transition layer composition is from about 5% w/w to about 70% w/w.

11. The moisture content indicator of claim 10, wherein the concentration of the opaque polymer in the transition layer composition is from about 20% w/w to about 45% w/w.

12. A method of applying a moisture content indicator onto a wood substrate comprising the steps of:
   (a) applying the moisture content indicator of claim 1 onto a wood substrate; and
   (b) allowing the transition layer composition of the moisture content indicator to dry.

13. The method of claim 12, wherein the transition layer composition further comprises one or more color pigments.

14. The method according to claim 12, wherein the wood substrate includes text and/or indicia incorporated into the wood substrate at the location that the moisture content indicator is applied to the wood substrate.

15. The method according to claim 14, wherein the text and/or indicia is indicative of the moisture content of the wood substrate.

16. The method of claim 12, wherein the moisture content indicator further comprises a moisture-permeable intermediate substrate upon which the transition layer composition is disposed prior to applying the moisture content indicator onto the wood substrate.

17. The method of claim 16, wherein the intermediate substrate includes an indicia that is incorporated or applied to the intermediate substrate at a location in alignment with the moisture content indicator.

18. The method of claim 16, wherein the intermediate substrate includes indicia applied to or incorporated thereon at a location in alignment with the location that the transition layer composition is applied to the intermediate substrate.

19. A method of making a wood product comprising the steps of:
   (a) applying a color layer composition comprising one or more colored pigment(s) and a color layer composition binding agent onto a wood substrate;
   (b) drying the color layer composition; and
   (c) applying the moisture content indicator of claim 1 onto the color layer composition.

20. The method of claim 19, wherein the transition layer composition further comprises one or more color pigments.

21. The method of claim 19, wherein the color layer composition is applied directly onto the wood substrate and the transition layer composition is applied directly onto the color layer composition.

22. The method of claim 19, wherein applying the color layer composition onto the wood substrate comprises applying the color layer composition onto a moisture-permeable intermediate substrate and applying the intermediate substrate having the color layer composition disposed thereon onto the wood substrate.

23. A wood product comprising:
   a wood substrate; and
   the moisture content indicator of claim 1 disposed on the wood substrate.

24. The wood product of claim 23, wherein the wood substrate is selected from the group consisting of oriented strand boards, plywood, particleboard, fiberboard, laminated veneer lumber, laminated strand lumber, oriented strand lumber, parallel strand lumber, long strand lumber, glulam, and solid sawn lumber.

25. The wood product of claim 23, wherein text and/or indicia is incorporated on or into the wood substrate at the location of the moisture content initiator.

26. The wood product of claim 25, wherein the text and/or indicia is indicative of the moisture content of the wood substrate.

27. The wood product of claim 23, further comprising a color layer composition disposed between the wood substrate and the transition layer composition of the moisture content indicator, said color layer composition comprising one or more colored pigment(s) and a color layer composition binding agent.

28. The wood product of claim 27, wherein the color layer composition binding agent is at least one of alkyd resin, an aqueous latex, and a polymeric or oligomeric dispersion.

29. The wood product of claim 27, wherein the wood substrate is selected from the group consisting of oriented strand boards, plywood, particleboard, fiberboard, laminated veneer lumber, laminated strand lumber, oriented strand lumber, parallel strand lumber, glulam, and solid sawn lumber.

30. The wood product of claim 27, wherein the color pigments of the color layer composition are arranged to form text and/or visual indicia in alignment with the transition layer composition, said text and/or visual indicia is visible when the substrate is of sufficiently high moisture content.

31. The wood product of claim 30, wherein said text and/or indicia is indicative of the moisture content of the wood substrate.

32. The wood product of claim 27, wherein the transition layer composition further comprises one or more color pigments.

* * * * *